United States Patent [19]
Boden et al.
[11] 4,436,652
[45] Mar. 13, 1984

[54] PHENYLETHYLMETHYLCARBONATE MIXTURES CONTAINING SAME AND ORGANOLEPTIC USES THEREOF

[75] Inventors: Richard M. Boden, Monmouth Beach; Theodore J. Tyszkiewicz, Sayreville; Hugh Watkins, Lincroft, all of N.J.

[73] Assignee: International Flavors & Fragrances Inc., New York, N.Y.

[21] Appl. No.: 422,489

[22] Filed: Sep. 23, 1982

Related U.S. Application Data

[62] Division of Ser. No. 329,221, Dec. 10, 1981.

[51] Int. Cl.[3] .......................... A61K 7/46; C11B 9/00
[52] U.S. Cl. .......................... 252/522 R; 252/8.6; 252/89.1; 252/182
[58] Field of Search .......................... 252/522 R

[56] References Cited

U.S. PATENT DOCUMENTS 3,959,508 5/1976 Pittet et al. .......... 252/522 R X
4,033,993 7/1977 Bruns et al. .......... 252/522 R X
4,080,309 3/1978 Bruns et al. .......... 252/522 R
4,217,253 8/1980 Schmitt .......... 252/522 J

*Primary Examiner*—Helen M. S. Sneed
*Attorney, Agent, or Firm*—Arthur L. Liberman

[57] ABSTRACT

Described is phenylethyl methylcarbonate having the structure:

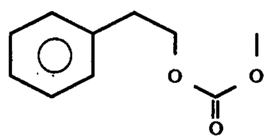

mixtures of same with 3-methyl-1-phenyl-pentanol-5 and/or one or more butanoyl cyclohexane derivative as well as processes and compositions for the use in perfume aroma augmenting, modifying, altering and enhancing compositions and as perfume, cologne and perfumed article aroma imparting materials of said phenylethyl methylcarbonate and mixtures thereof with 3-methyl-1-phenyl-pentanol-5 and/or one or more butanoyl cyclohexane derivatives.

3 Claims, 4 Drawing Figures

GLC PROFILE FOR FRACTION 6 OF EXAMPLE I.

MASS SPECTRUM FOR FRACTION 6 OF EXAMPLE I.

I R SPECTRUM FOR FRACTION 6 OF EXAMPLE I.

PHENYLETHYLMETHYLCARBONATE MIXTURES CONTAINING SAME AND ORGANOLEPTIC USES THEREOF

This is a divisional of application Ser. No. 329,221, filed Dec. 10, 1981.

BACKGROUND OF THE INVENTION

The present invention relates to phenylethyl methylcarbonate having the structure:

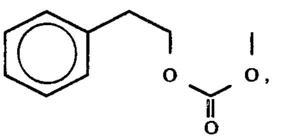

processes for preparing same and for preparing mixtures of same by reacting phenyl ethyl acetate with dimethyl carbonate in the presence of an alkalide metal alkoxide catalyst, and mixtures of phenylethyl methylcarbonate with other perfumery materials such as 3-methyl-1-phenyl-pentanol-5 and/or one or more butanoyl cyclohexane derivatives defined according to the following structures:

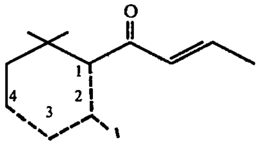

(generic structure) wherein one of the dashed lines is a carbon-carbon double bond or two of the dashed lines is a carbon-carbon double bond but that when the two of the dashed lines represents a carbon-carbon double bond the carbon-carbon double bonds are conjugated.

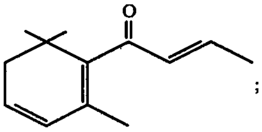
;

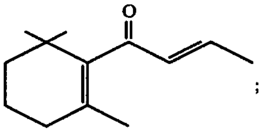
;

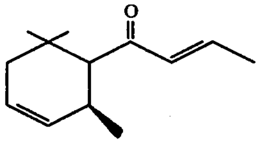

(wherein the dashed line represents a configuration of the butenoyl moiety "trans" with respect to the methyl moiety at the "two" position on the cyclohexane ring).

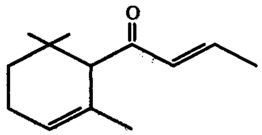

2,3-methyl-1-phenyl-pentanol-5:

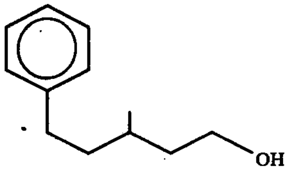

(representative of racemic mixture)

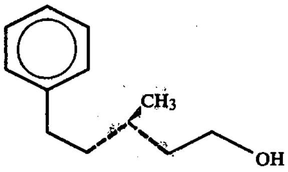

(steroisomer)

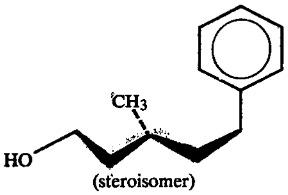

(steroisomer)

Materials which can provide natural rose nuances and which provide aroma profiles described as "rose, hyacinth, sweet powdery with fresh flower petal-like, fresh fruit and pineapple-like undertones" are highly desired in the art of perfumery. Provision of the "fresh petal-like" nuance is novel in the art of perfumery. Many of the natural substances which are alleged to provide rose fragrances and contributes certain of the desired nuances to perfumery compositions are high in cost, vary in quality from one batch to another and/or are generally subject to the usual variations of natural products.

The prior art contains a large number of teachings regarding the use of organic carbonates in augmenting or enhancing the aroma of perfumes.

Thus, U.S. Pat. No. 4,033,993 discloses the use of organic carbonates defined according to the structure:

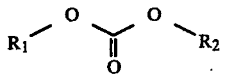

wherein $R_1$ is a moiety having from 8 to 12 carbon atoms selected from the group consisting of alkylcyclohexyl, alkenylcyclohexyl, alkynylcyclohexyl and cycloalkyl and $R_2$ is a moiety selected from the group consisting of alkyl having from 1 to 5 carbon atoms, alkenyl having from 2 to 5 carbon atoms and alkynyl having from 2 to 5 carbon atoms. U.S. Pat. No. 4,033,993 describes, for example, methyl-1-ethynycyclohexyl carbonate having a fruity, herbal and complex odor and distinct fragrance of dill. In addition, U.S. Pat. No. 4,033,993 describes methyl cyclooctyl carbonate as having an herbal, natural and complex fragrance which is distinguished by a strong and long clinging flowery jasmine scent and further indicates its use in jasmine perfume compositions. U.S. Pat. No. 4,033,993 describes the preparation of the compounds defined according to the structure:

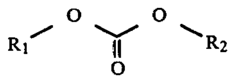

according to the reaction:

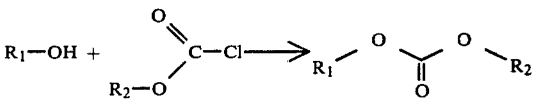

wherein $R_1$ and $R_2$ are defined as above.

In addition, U.S. Pat. No. 4,080,309 describes the perfume use of the carbonates defined according to the structure:

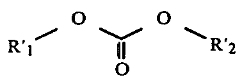

wherein $R_1'$ is a moiety having from 8 to 12 carbon atoms selected from the group consisting of alkylcyclohexyl, alkenylcyclohexyl, alkynylcyclohexyl and cycloalkyl and $R_2'$ is a moiety selected from the group consisting of alkyl having from 1 to 5 carbon atoms. Described in U.S. Pat. No. 4,080,309 are also such compounds as methyl cyclooctyl carbonate and the use thereof in jasmine perfume formulations. As is the case in U.S. Pat. No. 4,033,993, the carbonates of 4,080,309 are indicated to be prepared according to the reaction:

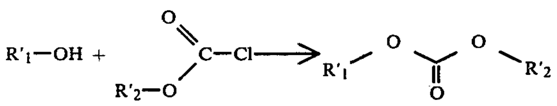

Arctander "Perfume & Flavor Chemicals (Aroma Chemicals)" published in 1969, at Volume 2, Monograph No. 2528 describes the chemical phenylethyl ethylcarbonate defined according to the structure:

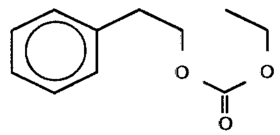

> "as pleasant etheral-alcohol-like, sweet and rather powerful odor of poor tenacity . . . The title material finds some use in perfume compositions as part of topnote compositions, floral bases and certain types of herbaceous fragrance. It blends well with Lavender and Clary Sage, and it has a mellowing effect upon the alifatic aldehydes and aldehydic topnote bases, etc.
>
> The ester is also interesting by its effect of "lifting" a musk odor so that the must becomes perceptible at a much earlier state of the perfume evaporation. In a way, the opposite of a fixative effect, but quite attractive when used with the proper amount and type of musk.
>
> Produced from Ethyl monochloroformate and Phenylethylalcohol in Chloroform with Pyridine as a catalyst."

In addition, U.S. Pat. No. 4,217,253 issued on Aug. 12, 1980, discloses processes and compositions for use in perfume aroma augmenting, modifying, altering and enhancing compositions and as perfume, cologne and perfumed article aroma imparting materials of mixtures of 3-methyl-1-phenyl-pentanol-5- and one or more butanoyl cyclohexane derivatives defined according to the following structures:

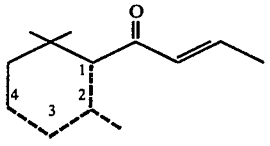

(generic structure) wherein one of the dashed lines is a carbon-carbon double bond or two of the dashed lines is a carbon-carbon double bond but that when the two of the dashed lines represents a carbon-carbon double bond the carbon-carbon double bonds are conjugated.

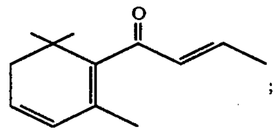

;

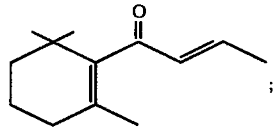

;

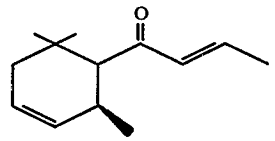

(wherein the dashed line represents a configuration of the butenoyl moiety "trans" with respect to the methyl moiety at the "two" position on the cyclohexene ring).

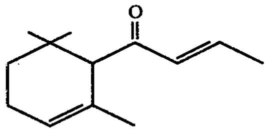

2,3-methyl-1-phenyl-pentanol-5:

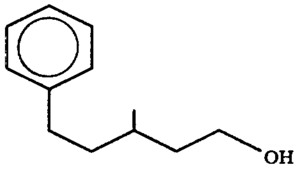

(representative of racemic mixture)

-continued

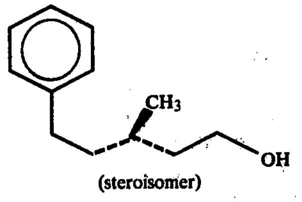

(steroisomer)

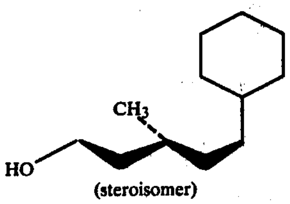

(steroisomer)

In addition, U.S. Pat. No. 4,028,279 entitled "Novel Fragrance Compositions Containing 2,6,6-Trimethyl-1-Cyclohexene-1-yl Acetaldehyde and Phenyl $C_6$ Ketone" relates to mixtures of (i) either or both of the phenyl $C_6$ ketones, 2,5-dimethyl-5-phenylhexanone-4 and 2,5-dimethyl-5-phenylhexen-1-one-3 and (ii) 2,2,6-trimethyl-cyclohexen-1-yl acetaldehyde used to alter, modify, enhance or impart aromas in or to perfumes, perfume compositions and/or perfumed articles. It is disclosed in said U.S. Pat. No. 4,028,279 that such perfume compositions containing such mixtures have intense rosey aromas with woody, green and earthy notes. The structure of the phenyl $C_6$ ketones disclosed in U.S. Pat. No. 4,208,279 is:

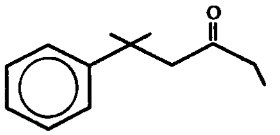

the structure of the betacyclohomocitral used in U.S. Pat. No. 4,028,279 is:

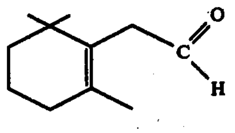

wherein the dashed line may be either a carbon-carbon single bond or a carbon-carbon double bond.

In U.S. Pat. No. 3,959,508, issued on May 25, 1976 mixtures of (i) 2,2,6-trimethyl-1-cyclohexen-1-yl acetaldehyde and (ii) 2,6,6-trimethyl crotonyl-1,3-cyclohexadiene having the structure:

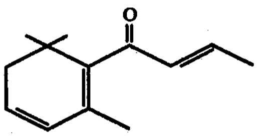

are indicated to produce in perfumes, rosey, woody, camphoraceous, green and earthy notes.

Nothing in the prior art including U.S. Pat. No. 3,959,508, 4,028,279, 4,217,253 or the Arctander reference implies or states that phenylethyl methylcarbonate or such mixtures as are disclosed and claimed in the instant case can be used to enhance and extend specific aroma nuances particularly in the rose and fresh petal aroma classification.

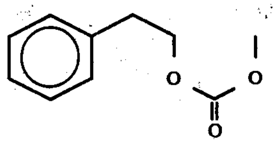

Figure 2:
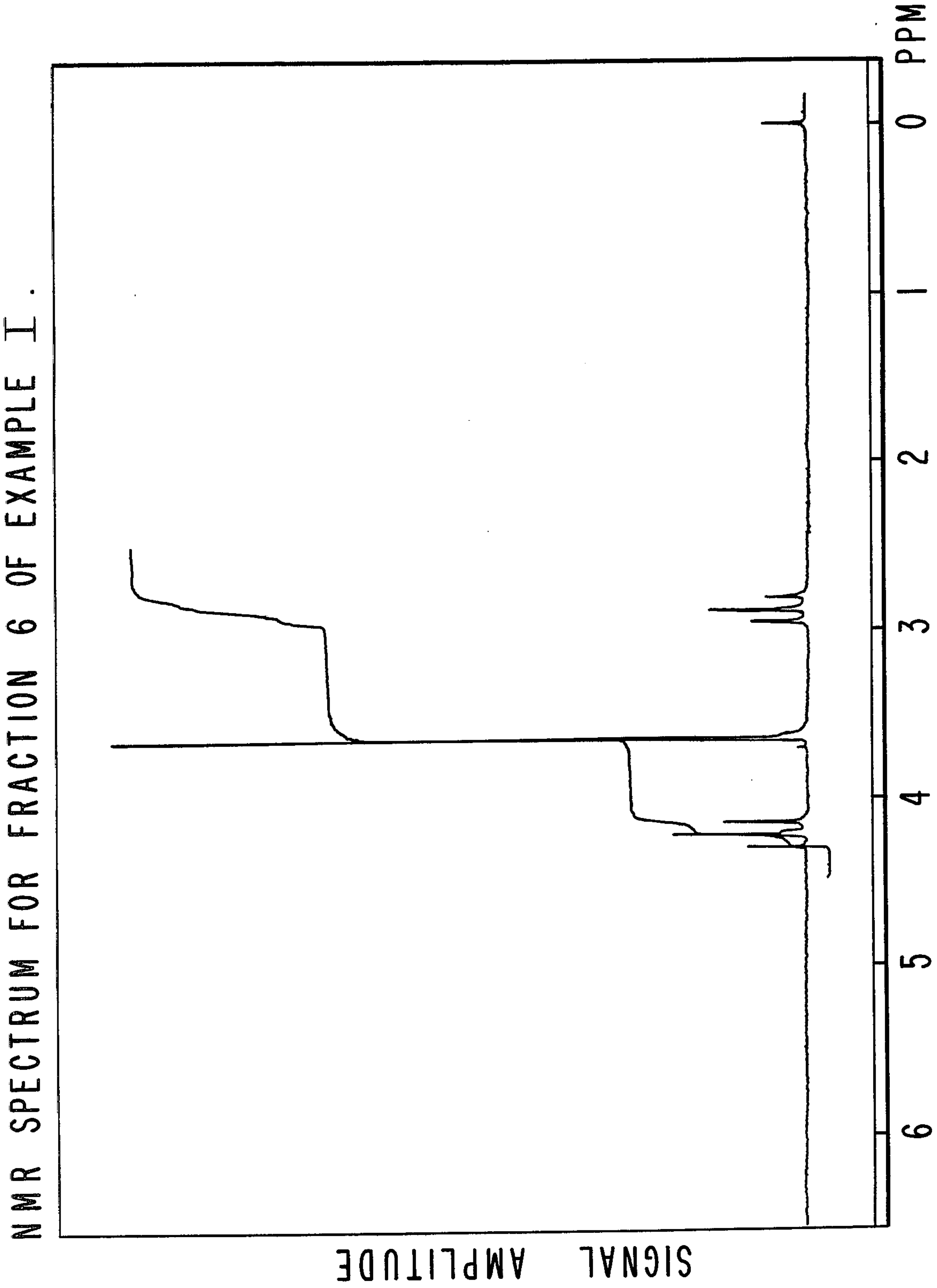

FIG. 2 is the NMR spectrum for fraction 6 of the distillation product of the reaction product of Example I containing the compound having the structure:

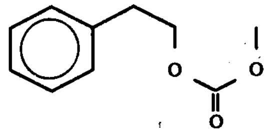

Figure 3:
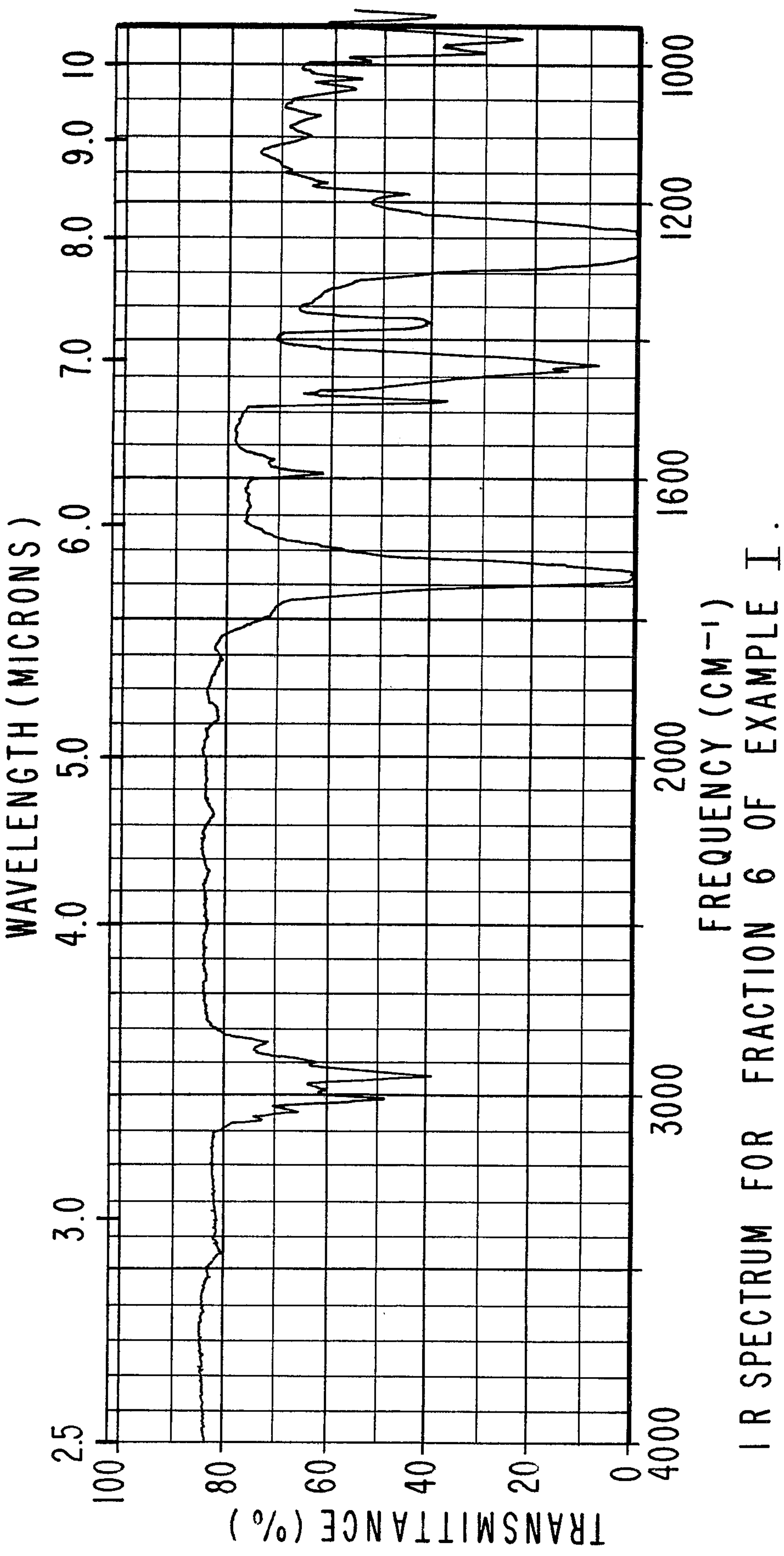

FIG. 3 is the infra-red spectrum for fraction 6 of the distillation product of the reaction product of Example I containing the compound having the structure:

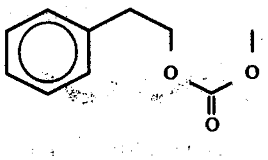

Figure 4:
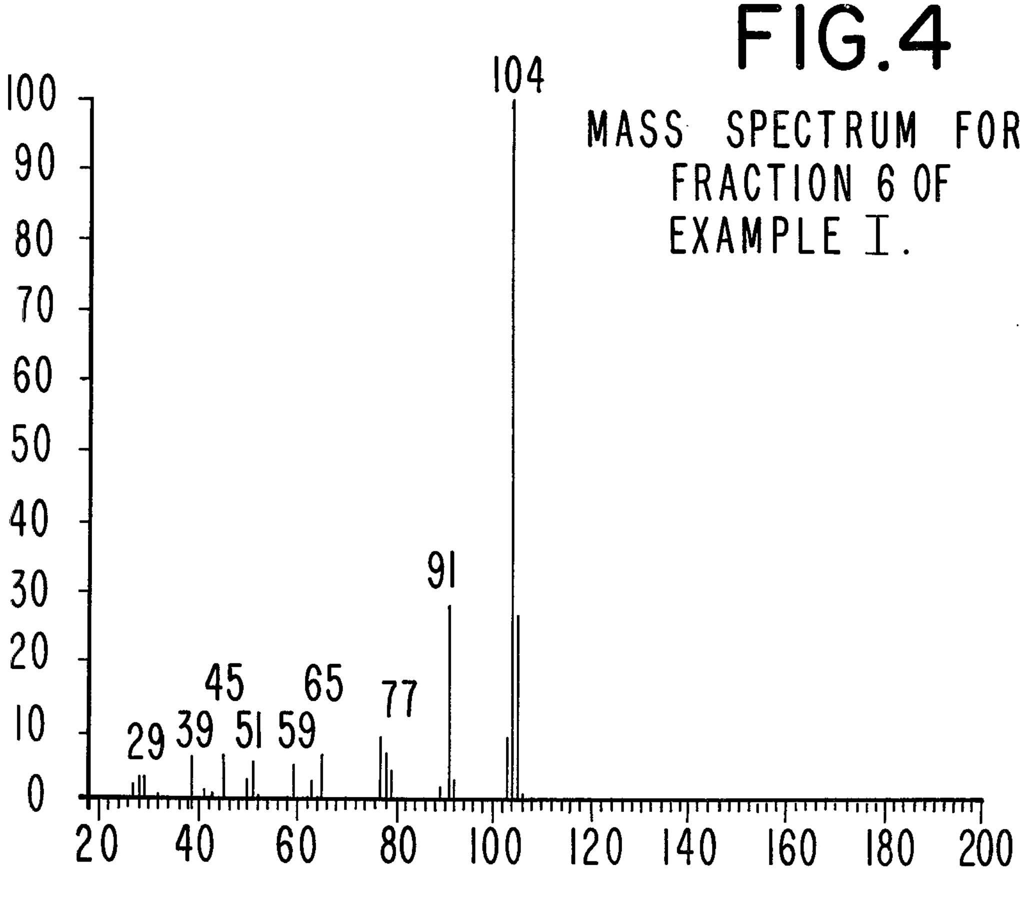

FIG. 4 is the mass spectrum of fraction 6 of the distillation product of the reaction product of Example I containing the compound having the structure:

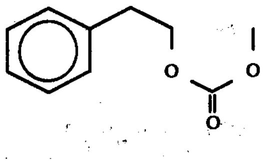

THE INVENTION

The present invention provides phenylethyl methylcarbonate defined according to the structure:

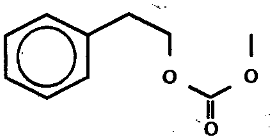

and mixtures of such phenylethyl methylcarbonate with (i) one or more butanoyl cyclohexane derivatives defined according to the structure:

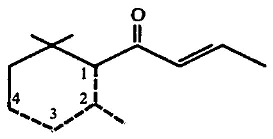

wherein one or two of the dashed lines is a carbon-carbon double bond and the other of the dashed lines are carbon-carbon single bonds with the proviso that if two of the dashed lines are carbon-carbon double bonds the carbon-carbon double bonds are conjugated and/or (ii) 3-methyl-1-phenyl-pentanol-5 racemic mixtures or individual stereoisomers having one of the structures:

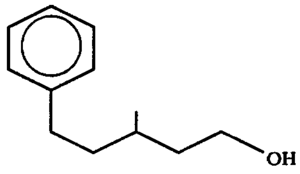

or

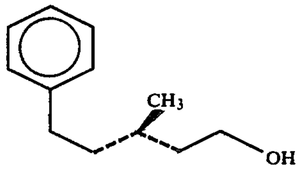

or

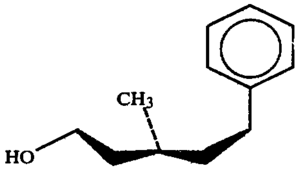

The present invention also provides an economical, efficient process for synthesizing phenylethyl methylcarbonate having the structure:

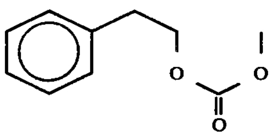

by reacting dimethyl carbonate with phenylethyl acetate in the presence of an alkali metal alkoxide according to the reaction:

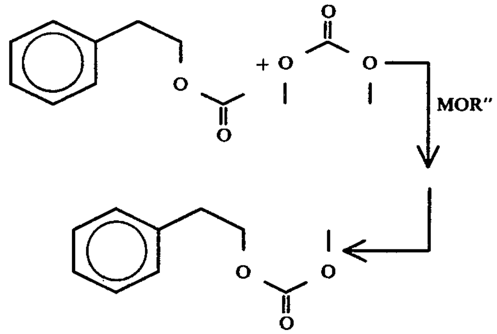

wherein M represents alkli metal such as sodium, potassium and lithium and wherein R'' represents lower alkyl such as methyl, ethyl, propyl, n-butyl and tertiary.

The present invention also provides processes for using phenylethyl methylcarbonate taken alone or taken together with (i) or more butanoyl cyclohexane derivatives as defined above and/or (ii) 3-methyl-1-phenyl-pentanol-5 racemic mixtures or individual stereoisomers thereof for their organoleptic properties in augmenting or enhancing the organoleptic properties of consumable materials, that is, the aroma of perfumes, colognes and perfumed articles (such as perfume polymers, solid or liquid cationic, anionic, nonionic or zwitterionic detergents, soaps, fabric softener compositions, drier-added fabric softener articles such as BOUNCE® registered trademark of the Procter & Gamble Company of Cincinnati, Ohio, fabric brighteners, cosmetic powders, bath preparations, hair preparations such as hair sprays and shampoos).

The phenylethyl methylcarbonate of our invention may be prepared by first reacting phenylethyl acetate with dimethyl carbonate according to the reaction:

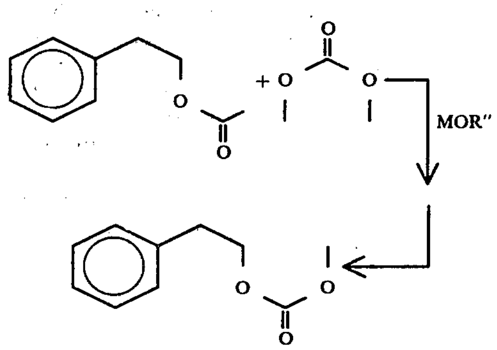

in the presence of an alkali metal alkoxide such as sodium methoxide, sodium ethoxide, sodium-t-butoxide, potassium methoxide, potassium ethoxide and potassium-t-butoxide. The reaction between the acetate ester and the dimethyl carbonate takes place in the absence of any additional solvent. The mole ratio range of dimethyl carbonate:acetate ester may vary from 3 moles dimethyl carbonate:0.5 moles acetate ester down to 1 mole dimethyl carbonate:1 mole acetate ester. It is preferred that the mole ratio of dimethyl carbonate:acetate ester be about 2:1. The molar concentration in the reaction mass of the alkali metal alkoxide catalyst may vary from about 0.005 up to about 0.01 with a mole ratio of about 0.05 being preferred.

The reaction temperature range may vary from about 50° C. up to about 100° C. and the reaction pressure may vary from atmospheric pressure up to about 10 atmospheres. Higher temperatures of reaction necessitate higher pressures over the reaction mass in order to prevent the reaction product from evaporating therefrom.

At the end of the reaction, the reaction product is purified according to standard procedures such as fractional distillation and, if necessary, chromatographic separation as by high pressure liquid chromatography or GLC (vapor phase chromatograph).

Unlike the phenylethyl methylcarbonate of the prior art the phenylethyl methylcarbonate of our invention can be used to contribute rose, hyacinth and sweet powdery aroma nuances with fresh flower petal-like, fresh fruit and pineapple-like undertones to perfume compositions, perfumed articles such as solid or liquid cationic, anionic, nonionic or zwitterionic detergents, perfumed polymers, fabric softener compositions, fabric softener articles, optical brighteners, fabric conditioners hair preparations, shampoos and hair sprays. As olfactory agents the phenylethyl methylcarbonate of our invention can be formulated into or used as components of a perfume composition. By the same token, mixtures of the phenylethyl methyl carbonate taken together with the butanoyl cyclohexane derivatives having the generic structure:

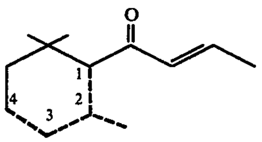

and/or the (ii) 3-methyl-1-phenyl-pentanol-5 racemic mixtures or individual stereoisomers thereof having one of the structures:

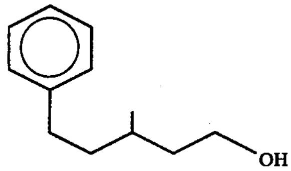

or

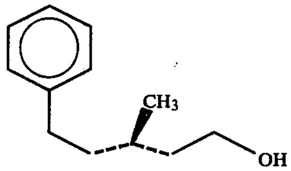

or

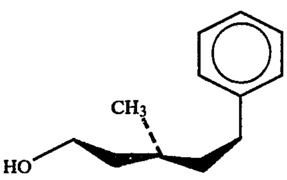

can be used to contribute rose, fresh flower petal-like aroma nuances to perfume compositions, perfumed articles such as solid or liquid cationic, anionic, nonionic or zwitterionic detergents, perfume polymers, fabric softener compositions, fabric softener articles, optical brighteners, fabric conditioners, hair preparations, shampoos and hair sprays. As olfactory agents the mixtures of phenylethyl methylcarbonate and the one or more of the butanoyl cyclohexane derivatives as defined, supra, and/or the 3-methyl-1-phenyl-pentanol-5 racemic mixtures or individual stereoisomers as defined, supra, of our invention can be formulated into or used as components of a "perfume composition".

The term "perfume composition" is used herein to mean a mixture of organic compounds including, for example, alcohols (other than the 3-methyl-1-phenyl-pentanol-5 racemic mixtures or individual stereoisomers thereof as defined above) aldehydes ketones (other than the butanoyl cyclohexane derivatives defined above), nitriles, ethers, lactones, esters other than the carbonates of our invention and frequently, hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main notes; (c) fixatives which include odorous substances which lend a particular note to the perfume throughout all stages of evaporation and substances which retard evaporation; and (d) topnotes which are usually low boiling, fresh smelling material.

In perfume compositions, the individual component will contribute its particular olfactory characteristics, but the overall effect of the perfume composition will be the sum of each of the effects of each of the ingredients. Thus, the individual compounds of this invention or mixtures thereof can be used to alter the aroma characteristics of the perfume composition, for example, by highlighting or moderating the olfactory reaction contributed by another ingredient in the composition.

The amount of phenylethyl methylcarbonate taken alone or taken further together with one or more of the butanoyl cyclohexane derivatives and/or the 3-methyl-1-phenyl-pentanol-5 of our invention which will be effective in perfume compositions depends upon many factors including the other ingredients, their amounts and the effects which are desired. It has been found that perfume compositions containing as little as 0.1% of the phenylethyl methylcarbonate taken alone or further together with one or more of the butanoyl cyclohexane derivatives defined above and/or the 3-methyl-1-phenyl-pentanol-5 isomers as defined above of our invention or even less in perfume compositions containing as much as 70% of the phenyl-ethyl methyl carbonate taken alone or further together with one or more butanoyl cyclohexane derivatives as defined above and/or one or more of 3-methyl-1-phenyl-pentanol-5 isomers as defined above can be used to impart interesting rosey, fresh flower petal-like aromas with additional hyacinth, sweet powdery, fresh fruit and pineapple-like nuances to perfumed articles, perfume compositions and colognes. Such perfumed articles include fabric softener compositions, drier-added fabric softener articles, cosmetic powders, talc, solid or liquid cationic, anionic, nonionic or zwitterionic detergent or such as a cosmetic powder as little as 0.01% of the phenylethyl methylcarbonate taken alone or further together with one or more of the butanoyl cyclohexane derivatives defined above and/or the 3-methyl-1-phenyl-pentanol-5 of our invention will suffice to provide an interesting rosey, hyacinth-like, sweet powdery aroma with fresh flower petal-like, fresh fruit, and pineapple-like undertones. Generally, no more than 0.8% of the phenylethyl methylcarbonate taken alone or further together with one or more butanoyl cyclohexane derivatives and/or the 3-methyl-1-phenyl-pentanol-5 of our invention are required.

Thus, the alkadienyl and cycloalkenyl methyl carbonates of our invention can be used alone or in a perfume composition as an olfactory component, in solid or liquid anionic, cationic, nonionic or zwitterionic detergents (including soaps), perfumed polymers (those which are microporous and those which are macroporous and contain particulate absorbent fillers such as talc), space odorants and deodorants; perfumes, colognes, toilet waters, bath salts, hair preparations such as lacquers, brilliantines, pomades and shampoos; cosmetic preparations such as creams, deodorants, hand lotions and sun screens; powders such as talcs, dusting powders, face powders and the like.

In addition, the perfume composition of our invention can contain a vehicle or carrier for the phenylethyl methylcarbonate taken alone or taken further together with one or more butanoyl cyclohexane derivatives and/or the 3-methyl-1-phenyl-pentanol-5 of our invention alone or with other ingredients. The vehicle can be a liquid such as an alcohol, such as ethanol, a glycol such as propylene glycol or the like. The carrier can be an absorbent solid such as a gum (e.g., xanthan gum or gum arabic) or components for encapsulating compositions such as by coacervation or by polymerization around a liquid center (for example using a urea formaldehyde pre-polymer).

The 3-methyl-1-phenyl-pentanol-5 described as having one of the structures:

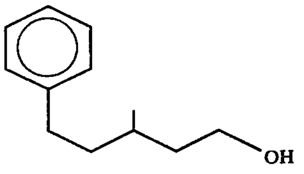

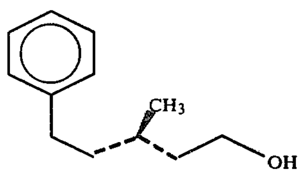

or

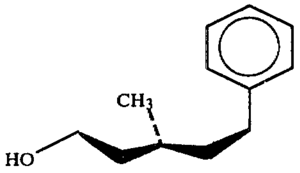

may be prepared according to the procedure described by Rupe Hirschmann and Werdenberg at Helv. 18 [1935] pages 535-542 (abstracted at Beilstein E III 6 1997, H 6,551).

Methods for preparing the butanoyl cyclohexane derivatives used in our invention are described in Swiss Pat. No. 520,479, issued on May 12, 1972 as well as application for U.S. patent application Ser. No. 851,727, filed on Nov. 15, 1977.

Contemplated within the scope of our invention are weight ratios of butanoyl cyclohexane derivative having the generic structure:

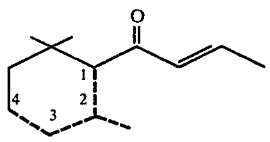

3-methyl-1-phenyl-pentanol-5 of from about $1\times10^{-7}$:1 up to about 0.1:1. It is however preferable in the practice of our invention to use weight ratios of butanoyl cyclohexane derivative:3-methyl-1-phenyl-pentanol-5 of from about $1\times10^{-7}$:1 up to about $5\times10^{-3}$:1 when using both the 3-methyl-1-phenyl-pentanol-5 and the butanoyl cyclohexane derivative.

Further contemplated within the scope of our invention are weight ratios of phenylethyl methylcarbonate:butanoyl cyclohexane derivative having the generic structure:

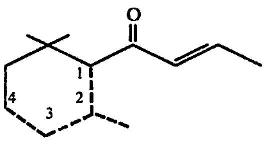

of from about 1:$1\times10^{-7}$ up to about 1:1. It is however preferable in the practice of our invention to use weight ratios of butanoyl cyclohexane derivative:phenyl ethyl methyl carbonate of from about $1\times10^{-6}$:1 up to about $5\times10^{-2}$:1.

When using the 3-methyl-1-phenyl-pentanol-5 of our invention together with phenylethyl methylcarbonate, also contemplated within the scope of our invention are weight ratios of phenylethyl methylcarbonate:3-methyl-phenyl-pentanol-5 of from about 0.1:1 up to about 1:10.1.

The following Example I sets forth the process for preparing phenyl ethyl methyl carbonate of our invention. The following Example II, et seq., represent methods for using the phenylethyl methylcarbonate taken alone or taken further together with the butanoyl cyclohexane derivatives and/or the 3-methyl-1-phenyl-pentanol-5 of our invention for their organoleptic properties.

Unless otherwise indicated, all parts and percentages are by weight.

EXAMPLE I

Process for Preparing Phenylethyl Methylcarbonate

Reaction:

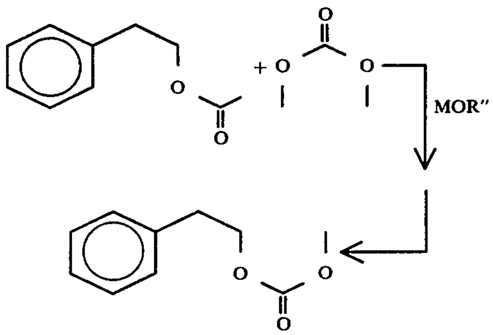

wherein M represents sodium and R" represents methyl.

Into a 2 liter reaction flask equipped with Bidwell trap, 1 liter addition funnel, stirrer, thermometer and reflux condenser and nitrogen atmosphere and nitrogen blanket apparatus is placed 32.4 grams (0.6 moles) of sodium methoxide; 720.6 grams (674 ml; 8 moles) dimethyl carbonate and 20 ml methyl acetate. The resulting mixture is heated to 80° C. and while maintaining the reaction mass at 80° C. over a period of 1 hour, 636 grams (4 moles) of phenyl ethyl acetate is added to the reaction mass. The reaction mass is then heated at 65°-83° C. for a period of 1 hour. At the end of the 1 hour period another 250 ml of dimethyl carbonate is added to the reaction mass, and the reaction mass is continued to be heated at 22°-87° C. for a period of 3 hours.

The reaction mass is then cooled to 30° C. and transferred to a separatory funnel. Two liters of saturated sodium chloride solution is added with stirring to the separatory funnel. The aqueous phase is separated from the organic phase and the organic phase is washed with 700 ml of a saturated sodium chloride solution. The combined aqueous layers are extracted with 100 ml of toluene and the extracts are combined and neutralized to a pH of 7. The resulting organic phases are then distilled on a 4 inch plash column packed with stones yielding the following fractions:

| Fraction No. | Vapor Temp. | Liquid Temp. | Head Vacuum mm.Hg | Weight of Fraction |
|---|---|---|---|---|
| 1 | 25/79 | 34/136 | 60/10 | 121 |
| 2 | 98 | 110 | 3 | 111 |
| 3 | 102 | 113 | 3 | 105 |
| 4 | 100 | 115 | 3 | 119 |
| 5 | 100 | 119 | 3 | 93 |
| 6 | 97 | 174 | 3 | 80 |
| 7 | 180 | 210 | 3 | 22 |

Figure 1:
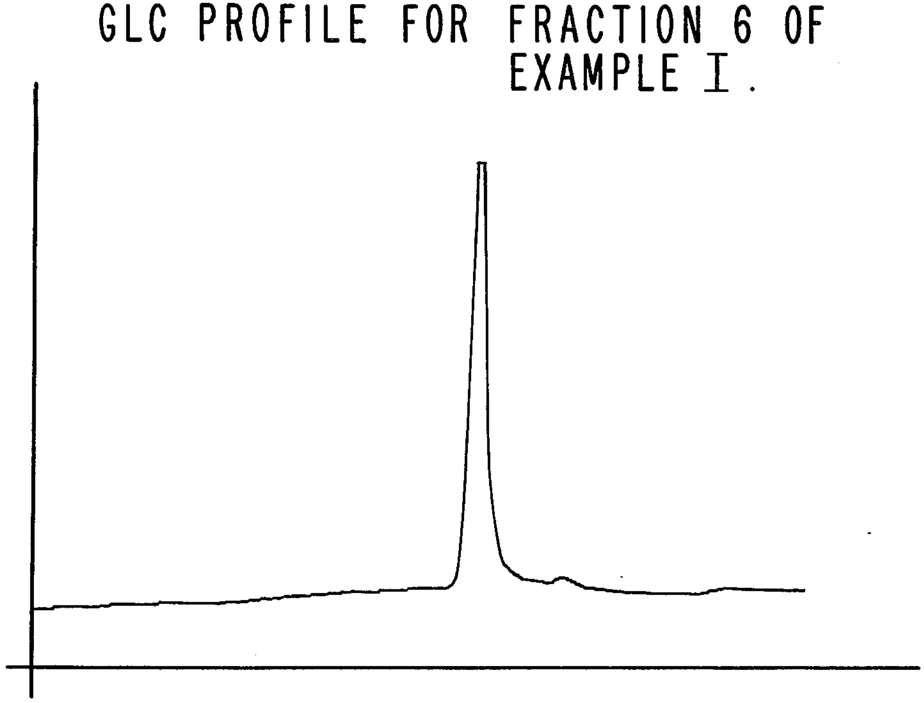
FIG. 1 is the GLC profile for fraction 6 of the distillation product of the reaction product of Example I containing the compound having the structure.

FIG. 1 is the GLC profile for fraction 6 of the foregoing distillation (conditions: 6'×¼", 12% SF-96 column programmed at 100°-220° C. at 8° C. per minute).

FIG. 2 is the NMR spectrum for fraction 6 of the foregoing distillation.

FIG. 3 is the Infra-red spectrum for fraction 6 of the foregoing distillation.

FIG. 4 is the mass spectrum for fraction 6 of foregoing distillation.

Fractions 5 and 6 are bulked and evaluated as having a rose, hyacinth, sweet powdery aroma with fresh flower petal-like, fruity and pineapple undertones.

EXAMPLE II

Rose Formulation

The following mixture is prepared:

| Ingredients | Parts by Weight |
|---|---|
| Rhodinol | 270.0 |
| Nerol | 90.0 |
| Linalool | 30.0 |
| Terpineol | 30.0 |
| Phenyl Ethyl Alcohol | 12.0 |
| Terpinenol | 5.0 |
| Linalyl Acetate | 1.5 |
| Citronellyl Acetate | 15.0 |
| Geranyl Acetate | 10.0 |
| Eugenol | 33.0 |
| Citral | 15.0 |
| Phenyl Ethyl Acetate | 20.0 |
| Rose Oxide | 8.0 |
| Guaiacol | 30.0 |
| 1-citronellal | 90.0 |
| Neryl Acetate | 3.0 |
| Clove Bud Oil | 1.0 |
| Cadinene | 2.0 |
| Guaiene | 1.0 |
| Gum Terpentine | 12.0 |
| Alpha-piene | 1.0 |
| Myrcene | 5.0 |
| Limonene | 2.0 |
| p-cymene | 1.0 |
| | 687.5 |

The foregoing formulation is divided into four parts, Parts A, B, C and D.

To Part A, 30 parts by weight of a 0.1% solution of phenylethyl methylcarbonate in diethyl phthalate is added.

To Part B, 30 parts by weight of a mixture of a 0.1% solution of 3-methyl-1-phenyl-pentanol-5 in diethyl phthalate and 30 parts by weight of a 0.01% solution of phenylethyl methylcarbonate is added.

To Part C, 30 parts by weight of a mixture of 0.1% solution of phenylethyl methylcarbonate in diethyl phthalate; 30 parts by weight of a 0.1% solution of 3-methyl-1-phenyl-pentanol-5 in diethyl phthalate; and 15 parts by weight of a mixture of a 0.01% solution of beta damascenone and diethyl phthalate is added.

To Part D, 30 parts by weight of a mixture of 0.1% solution of phenylethyl methylcarbonate in diethyl phthalate; 30 parts by weight of 0.1% solution of 3-methyl-1-phenyl-pentanol-5 and diethyl phthalate and 15 parts by weight of 0.01% solution of beta damascenone and diethyl phthalate is added.

Each of the resultant mixtures; parts A, B, C and D have much brighter, rose topnotes and are fruiter and richer on dry-out; and unexpectedly have fresh flower petal-like nuances which are very long lasting and intense as compared with the same mixture without the compositions of matter containing the phenylethyl methylcarbonate (bulked fractions 5 and 6) produced according to Example I, supra.

EXAMPLE III

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
|---|---|
| Phenylethyl methylcarbonate prepared according to Example I, bulked fractions 5 and 6 | A rose, hyacinth and sweet powdery aroma with fresh flower petal-like, fresh fruit and pineapple-like undertones. |
| 50:50 (wgt:wgt) mixture of phenylethyl methylcarbonate produced according to Example I, bulked fractions 5 and 6 and 3-methyl-1-phenyl-pentanol-5 isomer mixture | An interesting warm fruity, rose aroma with intense rose petal, fruity pineapple-like nuances lasting for 5 weeks. |
| Mixture containing 0.1% (by wgt.) of beta damascenone in a 50:50 mixture (wgt:wgt) of 3-methyl-1-phenyl-pentanol-5 and phenylethyl methylcarbonate prepared according to Example I, bulked fractions 5 and 6 | An intense rose aroma with warm fruity, fresh rose petal-like undertones. |
| Mixture containing 0.2% beta damascenone in 50:50 mixture of 3-methyl-1-phenyl-pentanol-5: phenylethyl methylcarbonate | A rosey, warm fruity aroma with intense rose petal-like pineapple-like undertones lasting for 4 weeks. |
| Mixture containing 0.5% trans, trans delta damascone in phenylethyl methylcarbonate | A rose, hyacinth, powdery aroma with intense rose petal-like and fruity undertones. |
| Mixture containing 0.5% trans, trans delta damascone in a 25:75 (wgt:wgt) mixture of 3-methyl-1-phenyl-pentanol-5: phenylethyl methylcarbonate | A warm fruity, flower petal note with a rose body and a powerful rose flower petal topnote lasting for 8 weeks. |
| Perfume composition of either of Example IIa, IIb, IIc or IId | An intense rose aroma with interesting warm fruity, hyacinth, powdery, flower petal-like and fruity under- |

TABLE I-continued

| Substance | Aroma Description |
|---|---|
| | tones. |

EXAMPLE IV

Perfumed Liquid Detergents

Concentrated liquid detergents (Lysine salt of n-dodecylbenzene sulfonic acid as more specifically described in U.S. Pat. No. 3,948,818, issued on Apr. 6, 1976 incorporated by reference herein) with aroma nuances as set forth in Table I of Example III are prepared containing 0.10%, 0.15%, 0.20%, 0.25%, 0.30% and 0.35% of the substance set forth in Table I of Example III. They are prepared by adding and homogeneously mixing the appropriate quantity of substance set forth in Table I of Example III in the liquid detergent. The detergents all possess excellent aromas as set forth in Table I of Example III, the intensity increasing with greater concentrations of substance as set forth in Table I of Example III.

EXAMPLE V

Preparation of Colognes and Handkerchief Perfumes

Compositions as set forth in Table I of Example III, are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example III are imparted to the colognes and to the handkerchief perfumes at all levels indicated.

EXAMPLE VI

Preparation of Soap Compositions

One hundred grams of soap chips [per sample] (IVORY ®, produced by the Procter & Gamble Company of Cincinnati, Ohio), are each mixed with one gram samples of substances as set forth in Table I of Example III until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example III.

EXAMPLE VII

Preparation of Solid Detergent Compositions

Detergents are prepared using the following ingredients according to Example I of Canadian Pat. No. 1,007,948 (incorporated by reference herein):

| Ingredient | Percent by Weight |
|---|---|
| "Neodol ® 45-11" (a $C_{14}$-$C_{15}$ alcohol ethoxylanted with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example III. Each of the detergent samples has an excellent aroma as indicated in Table I of Example III.

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:

1. A water "dissolvable" paper ("Dissolvo Paper")
2. Adogen 448 (m.p. about 140° F.) as the substrate coating; and
3. An outer coating having the following formulation (m.p. about 150° F.):
   57% $C_{20-22}$ HAPS
   22% isopropyl alcohol
   20% anti-static agent
   1% of one of the substances as set forth in Table I of Example III.

Fabric softening compositions prepared according to Example I at column 15 of U.S. Pat. No. 3,632,396 having aroma characteristics as set forth in Table I of Example III, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example III is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table I of Example III, supra.

EXAMPLE IX

Hair Spray Formulations

The following hair spray formulation is prepared by first dissolving PVP/VA E-735 copolymer manufactured by the GAF Corporation of 140 West 51st Street, New York, New York, in 91.62 grams of 95% food grade ethanol. 8.0 grams of the polymer is dissolved in the alcohol. The following ingredients are added to the PVP/VA alcoholic solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| Tween 20 surfactant (prepared by ICI America Corporation) | 0.03 weight percent |
| One of the perfumery substances as set forth in Table I of Example III, supra | 0.10 weight percent |

The perfuming substances as set forth in Table I of Example III add aroma characteristics as set forth in Table I of Example III which are rather intense and asethetically pleasing to the users of the soft-feel, good-hold pump hair sprays.

EXAMPLE X

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

Gafquat® 755 N polymer (manufactured by GAF Corporation of 140 West 51st Street, New York, New York) (5.0 weight percent) is admixed with 0.1 weight percent sodium sulfite and 1.4 weight percent polyethylene glycol 6000 distearate produced by Armak Corporation. This material is "COMPOSITION B".

The resulting COMPOSITION A & COMPOSITION B are then mixed in a 50:50 wt ratio of A:B and cooled to 45° C. and 0.3 wt percent of perfuming substance as set forth in Table I of Example III is added to the mixture. The resulting mixture is cooled to 40° C. and blending is carried out for an additional one hour in each case. At the end of this blending period, the resulting material has a pleasant fragrance as indicated in Table I of Example III.

When the phenylethyl methylcarbonate of our invention is prepared by means of a process other than reacting phenyl ethyl acetate with dimethyl carbonate, for example, when reacting phenyl ethyl alcohol with dimethyl carbonate according to the reaction:

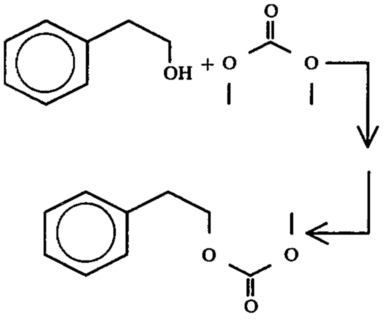

the intense flower petal nuance is completely lacking. Indeed, no fresh fruity petal notes exist in the resulting product. Thus, the process for preparing the phenylethyl methylcarbonate having the structure:

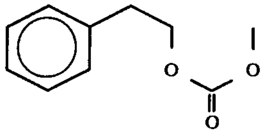

according to the reaction:

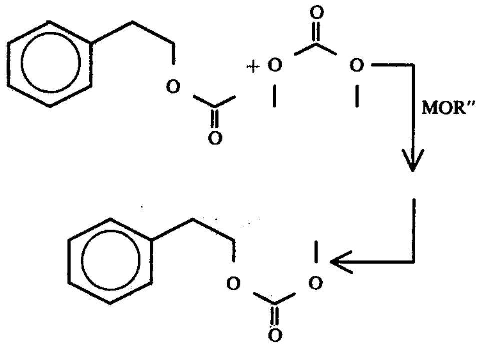

is important to the properties of the ultimate product produced.

What is claimed is:

1. A mixture consisting essentially of phenylethyl methylcarbonate having the structure:

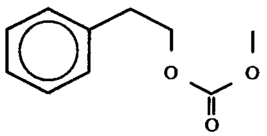

and at least one substance selected from the group consisting of:

(i) 3-Methyl-1-phenyl-pentanol-5 or stereoisomers thereof having a structure selected from the group consisting of:

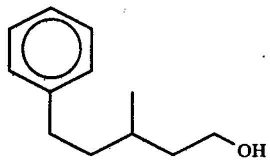

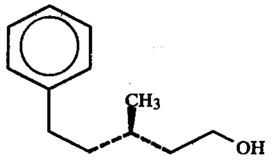

and,

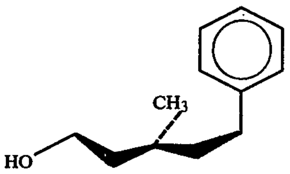

the weight ratio of phenylethyl methylcarbonate:3-methyl-1-phenyl-pentanol-5 being from about 0.1:1 up to about 1:0.1; and (ii) at least one cyclohexyl butenone derivative defined according to the structure:

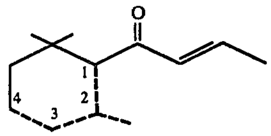

wherein one or two of the dashed lines is a carbon-carbon double bond and the other of the dashed lines is a carbon-carbon single bond with the proviso that when two of the dashed lines are carbon-carbon double bonds, said carbon-carbon double bonds are conjugated, the weight ratio of phenylethyl methylcarbonate:cyclohexyl butenone derivative having the generic structure:

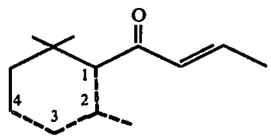

being from about $1:1\times10^{-7}$ up to about 1:1.

2. A process for augmenting or enhancing the aroma of consumable materials selected from the group consisting of perfume compositions, colognes and perfumed articles comprising the step of adding to a perfume composition or cologne an aroma augmenting or enhancing quantity of the composition of matter of claim 1.

3. The process of claim 2 wherein the consumable material is a perfume composition or cologne.

* * * * *